United States Patent
Glen et al.

(10) Patent No.: US 11,931,249 B2
(45) Date of Patent: Mar. 19, 2024

(54) EASY VOICE PROSTHESIS LOADING INSERTION DEVICE

(71) Applicant: Freudenberg Medical, LLC, Carpinteria, CA (US)

(72) Inventors: Kevin Alan Glen, Ventura, CA (US); Dimitrios Stroumpoulis, Santa Barbara, CA (US)

(73) Assignee: Freudenberg Medical, LLC, Carpinteria, CA (US)

(*) Notice: Subject to any disclaimer, the term of this patent is extended or adjusted under 35 U.S.C. 154(b) by 409 days.

(21) Appl. No.: 17/340,527

(22) Filed: Jun. 7, 2021

(65) Prior Publication Data
US 2022/0387172 A1   Dec. 8, 2022

(51) Int. Cl.
*A61F 2/20*   (2006.01)
*A61B 17/24*   (2006.01)
*A61B 17/34*   (2006.01)

(52) U.S. Cl.
CPC ............... *A61F 2/20* (2013.01); *A61B 17/24* (2013.01); *A61B 17/3468* (2013.01)

(58) Field of Classification Search
CPC .......................... A61F 2/203; A61B 17/24
See application file for complete search history.

(56) References Cited

U.S. PATENT DOCUMENTS

| | | | |
|---|---|---|---|
| 5,935,165 A * | 8/1999 | Schouwenburg | A61F 2/203 623/9 |
| 8,721,720 B2 | 5/2014 | Margolin et al. | |
| 9,320,596 B2 | 4/2016 | Margolin et al. | |

(Continued)

FOREIGN PATENT DOCUMENTS

| | | | | |
|---|---|---|---|---|
| DE | 102017103623 | * | 5/2018 | ............. A61F 2/203 |
| DE | 102017103623 B3 | | 5/2018 | |

(Continued)

OTHER PUBLICATIONS

Extended European Search Report dated Oct. 17, 2022 (corresponding to EP 22169903.6).

(Continued)

*Primary Examiner* — Jerrah Edwards
*Assistant Examiner* — Anasia A Summersett
(74) *Attorney, Agent, or Firm* — Daniel J. Sepanik, Esq.; Harness, Dickey & Pierce, P.L.C.

(57) ABSTRACT

A voice prosthesis insertion device includes an elongated body having an aperture therein extending axially along the elongated body. The elongated body includes a ring member at one end that is supported by a pair of straps. The elongated body has at least one region that is increasing in cross section. The elongated body further having a collapsible portion defined by a pair of openings in the elongated body. A rod is disposed in the aperture of the elongated body and including a peg adapted to be inserted into an aperture of a tether of a voice prosthesis device. The collapsible portion of the elongated body is flexible to allow the collapsible portion to be longitudinally collapsed to expose the peg of the rod for easy engagement with the strap of the voice prosthesis and the collapsible portion is extendable from the collapsed position to extend over the peg.

9 Claims, 4 Drawing Sheets

(56) References Cited

U.S. PATENT DOCUMENTS

2009/0036983 A1\* 2/2009 Tran ................ A61F 2/203
                                                606/108
2011/0093071 A1\* 4/2011 Blom ............... A61F 2/203
                                                  623/9
2020/0368013 A1\* 11/2020 Fahl ............... A61F 2/203

FOREIGN PATENT DOCUMENTS

WO      2005097001 A1    10/2005
WO   WO-2005097001 A1 \* 10/2005  ............ A61F 2/203

OTHER PUBLICATIONS

1 Canadian Office Action dated Jun. 15, 2026 (corresponding to CA 3156960).

\* cited by examiner

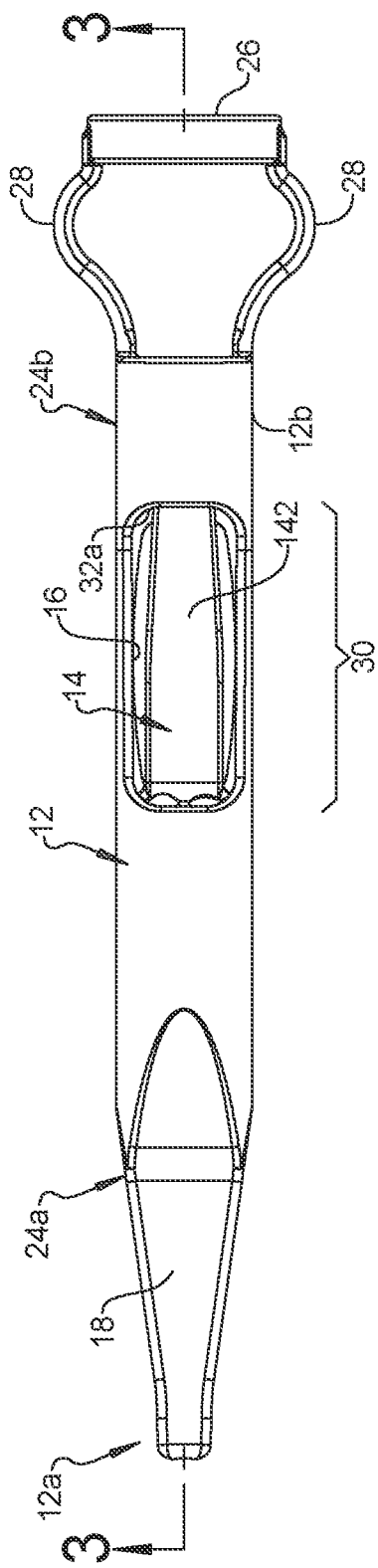
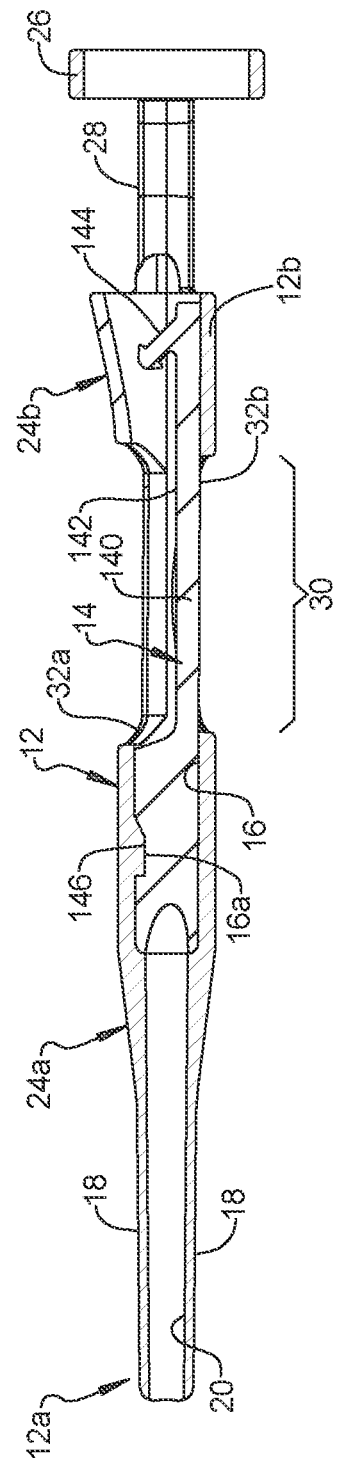

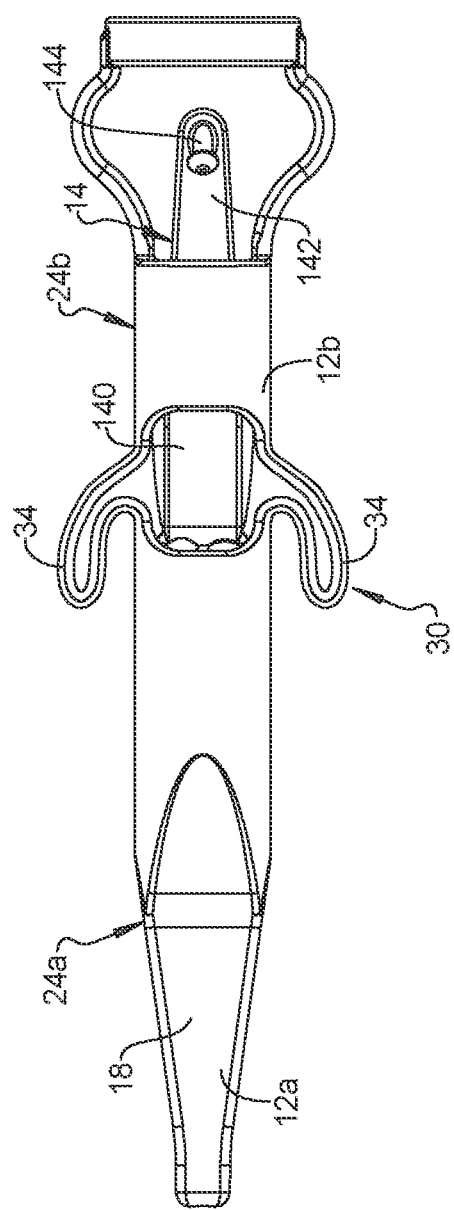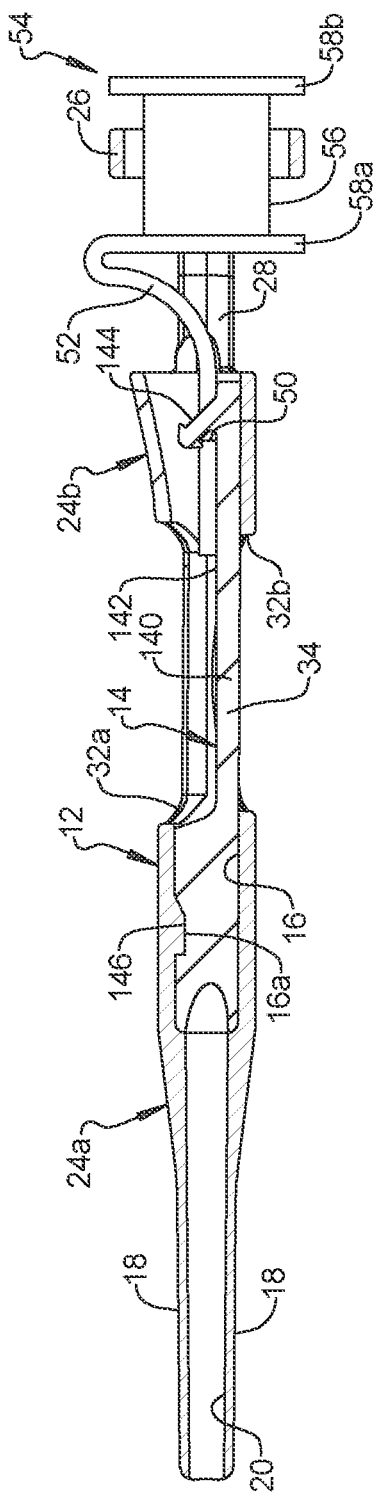

EASY VOICE PROSTHESIS LOADING INSERTION DEVICE

FIELD

The present disclosure relates to a voice prosthesis insertion device and more particularly to a voice prosthesis insertion device in which a voice prosthesis can be easily loaded.

BACKGROUND

This section provides background information related to the present disclosure which is not necessarily prior art.

During a total laryngectomy, the larynx is removed and two separate pipes are created for swallowing and breathing/talking. The mouth is connected to the esophagus, forming one pipe for swallowing. The trachea is redirected to create a permanent hole on the surface of the neck, forming one pipe for breathing. This hole is called a tracheostoma (TRAY-kee-oh STOW-ma), or "stoma" for short. The nose and the mouth do not connect to the lungs after this surgery.

It has been known to provide a tracheoesophageal prosthesis (or voice prosthesis) to restore people's ability to speak after a laryngectomy. Tracheoesophageal (TE) speech tends to be easier to produce and learn than esophageal speech and sounds more natural than using an electrolarynx. A small hole or puncture is made in the common wall between the trachea and the esophagus. This puncture is visible inside the stoma and becomes a path to allow airflow into the esophagus. The voice prosthesis is inserted in the puncture to keep it open and includes a small silicone one-way valve. The voice prosthesis also keeps food and liquid from flowing from the esophagus into the trachea. The voice prosthesis is typically surgically installed.

The present disclosure recognizes that an improved voice prosthesis insertion device is needed to allow for easier loading and installing of the voice prosthesis.

SUMMARY

This section provides a general summary of the disclosure, and is not a comprehensive disclosure of its full scope or all of its features.

A voice prosthesis insertion device includes an elongated body having an aperture therein extending axially along the elongated body. The elongated body includes a ring member at one end that is supported by a pair of straps. The elongated body has at least one region that is increasing in cross-section. The elongated body further having a collapsible portion defined by a pair of openings in the elongated body. A rod is disposed in the aperture of the elongated body and including a peg adapted to be inserted into an aperture of a tether of a voice prosthesis device. The collapsible portion of the elongated body is flexible to allow the collapsible portion to be longitudinally collapsed to expose the peg of the rod for easy engagement with the strap of the voice prosthesis and the collapsible portion is extendable from the collapsed position to extend over the peg.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2 is a top plan view of the voice prosthesis inserter device according to the principles of the present disclosure;

FIG. 3 is a longitudinal cross sectional view of the voice prosthesis inserter device taken along line 3-3 of FIG. 2;

FIG. 6 is a top plan view of the voice prosthesis inserter device shown with the collapsible portion in folded/retracted position; and FIG. 7 is a longitudinal cross sectional view of the voice prosthesis inserter device illustrating a voice prosthesis device loaded therein.

Corresponding reference numerals indicate corresponding parts throughout the several views of the drawings.

DETAILED DESCRIPTION

Figure 1:
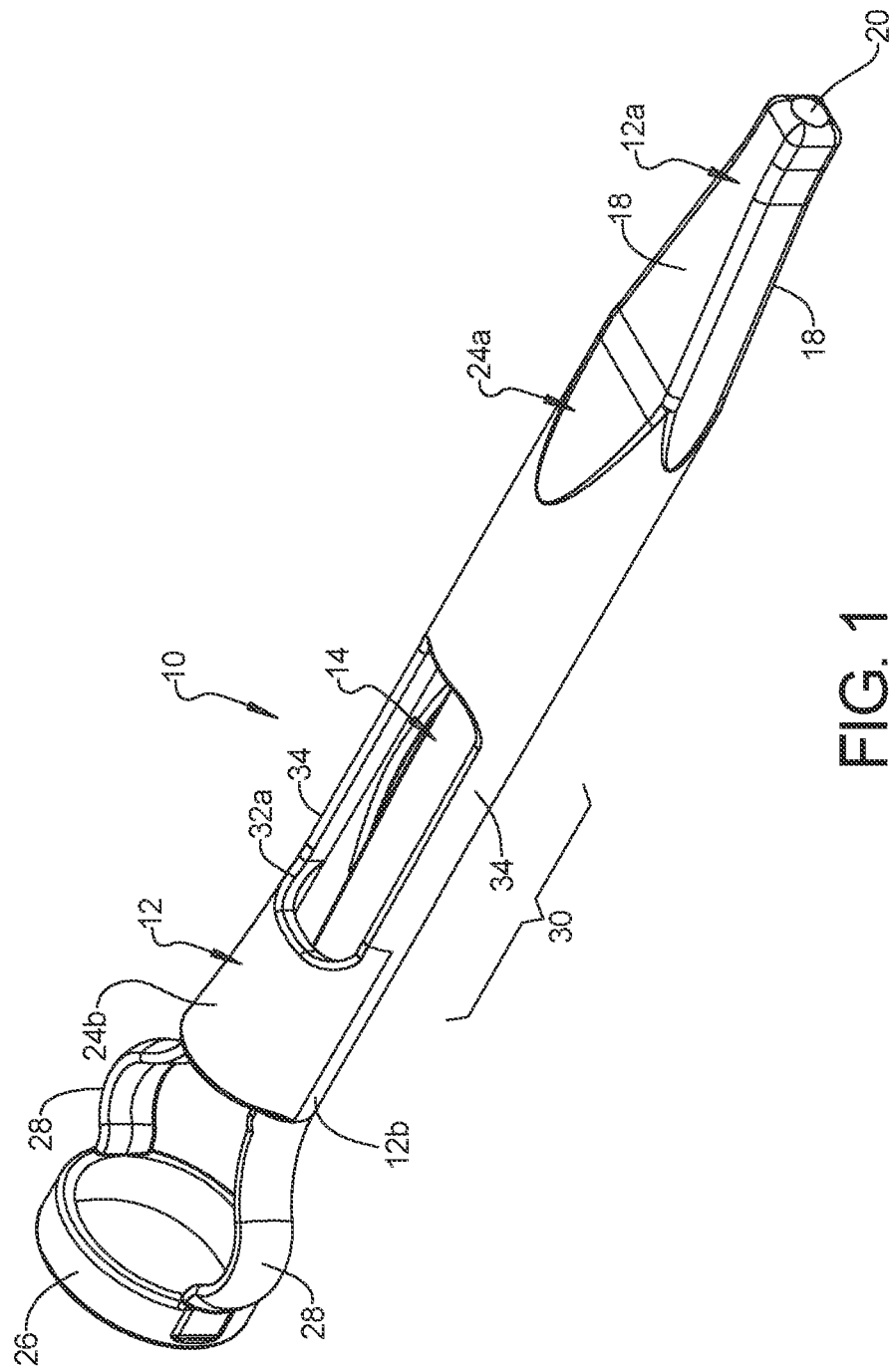
FIG. 1 is a perspective view of a voice prosthesis inserter device according to the principles of the present disclosure.
Figure 4:
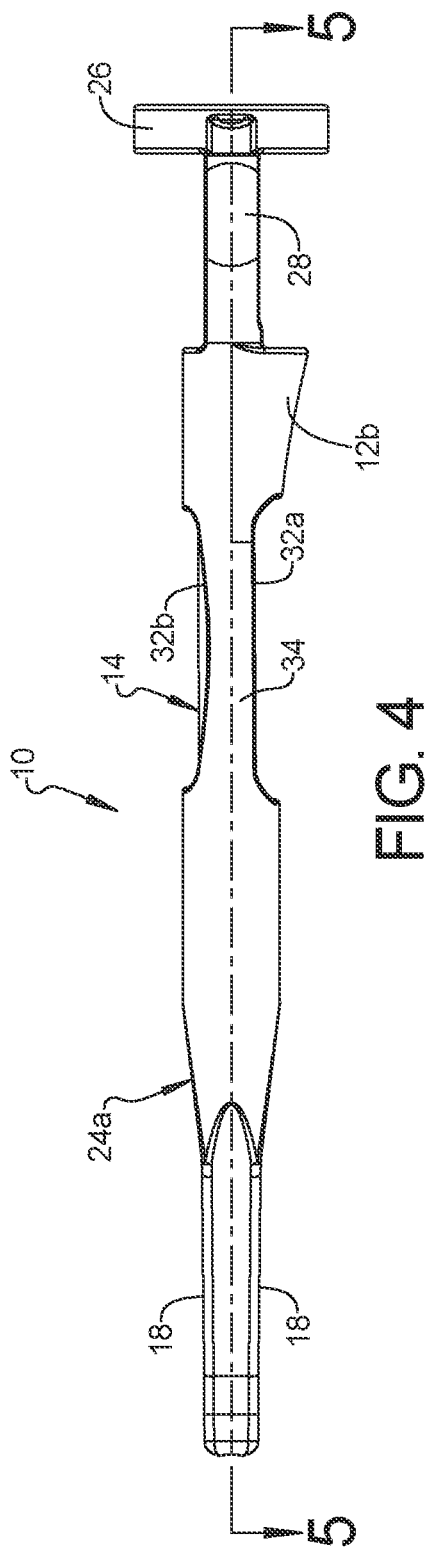
FIG. 4 is a side plan view of the voice prosthesis inserter device according to the principles of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

With references to FIGS. 1-5, a voice prosthesis inserter device 10 is shown including an elongated inserter body 12 and a peg rod 14 (best shown in FIG. 3), inside of an longitudinal aperture 16 in the elongated inserter body 12. The elongated inserter body 12 is made from a flexible material and includes a first end 12a having a pair of flats 18 that provide a grip for improved manipulation by a user. A hole 20 is in communication with the longitudinal aperture 16 is provided in the first end 12a for receiving a cable or stringer, not shown. The elongated inserter body 12 includes at least one tapering region 24a, 24b that increases in diameter toward a second end 12b of the elongated inserter body 12. In the embodiment shown, two tapering regions 24a, 24b are shown. The elongated inserter body 12 further includes a ring 26 that is supported by a pair of outwardly curved straps 28 that are also connected to the tapering region 24b.

Figure 5:
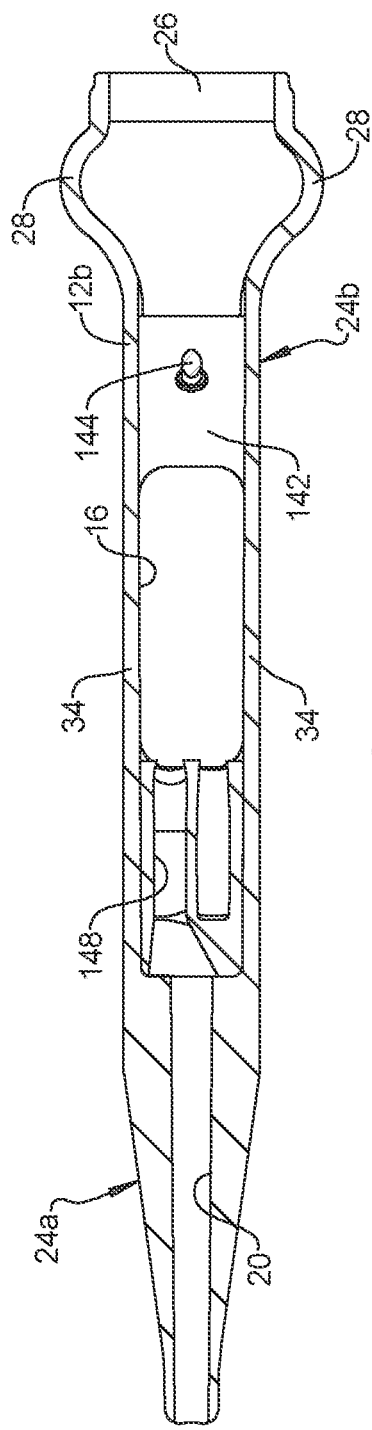
FIG. 5 is a longitudinal cross sectional view of the voice prosthesis inserter device taken along line 5-5 of FIG. 4.

With reference to FIG. 3, the peg rod 14 includes an elongated body 140 having a flat region 142 at one end with a peg 144 extending from the flat region 142. The elongated body 140 further includes a recess region 146 (best shown in FIG. 7) that is engaged by a retainer projection 16a within the aperture 16 of the elongated inserter body 12. As shown in FIG. 5, the peg rod 14 further includes a stringer attachment feature 148 for receiving a stringer (not shown). The stringer can include a flexible plastic strand that can be bent into a hook at one end for engaging with the stringer attachment feature 148 and then pass through the hole 20. The elongated inserter body 12 captures the hook shaped end of the stringer within the stringer attachment feature.

The elongated inserter body further includes a collapsible portion 30 disposed adjacent to the tapering region 24b and distal to the pair of outwardly curved straps 28. The collapsible portion 30 is defined by a pair of opposed openings 32a, 32b that are separated by a pair of collapsible sidewall portions 34. The opposed openings 32a, 32b can be different sizes or of the same size and they are designed to provide the elongated inserter body with the ability to collapse longitudinally as shown in FIG. 6 where the collapsible sidewall portions 34 are folded over themselves to allow the tapering region 24b to be longitudinally retracted in order to expose the peg 144 and flat region 142 of the peg rod. When the peg 144 of the peg rod 14 is exposed with the tapering region 24b longitudinally retracted, a user is able to insert the peg 144 into an opening 50 in a tether 52 of a voice prosthesis device 54, best shown in FIG. 7.

In FIG. 7, the voice prosthesis 54 is shown with the opening 50 of the tether 52 engaged with the peg 144 and the collapsible portion 30 in an un-deformed state so that the tapering region 24b is covering the peg 144 and the ring 26 is disposed around the tubular body 56 and between the flanges 58a, 58b of the voice prosthesis 54 so that the voice prosthesis insertion device 10 is loaded and ready for use. In use, a tracheoesophageal puncture is surgically created between the esophagus and trachea of a patient. A stringer can be passed through the tracheoesophageal puncture and accessed through the patient's mouth. The stringer is then fed through the hole 20 in the elongated inserter body 12 and connected to the voice prosthesis insertion device 10 by engaging the stringer to the stringer attachment feature 148 of the peg rod 14. The stinger can then be used to pull the voice prosthesis insertion device 10 through the patient's mouth, along the esophagus and out through the tracheoesophageal puncture where the voice prosthesis is deployed with the flange 58b on the esophagus side and the flange 58a and tether 52 on the trachea side. The tracheoesophageal puncture is accessible through a stoma in the patient's neck.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A voice prosthesis insertion device, comprising:
   an elongated inserter body having a first end and a second end and including an aperture therein extending axially along the elongated inserter body, the elongated inserter body including a ring member at the second end that is supported by a pair of straps, the elongated inserter body having a collapsible portion; and
   a rod disposed in the aperture of the elongated inserter body, the rod including a first end and a second end and the second end including a peg extending therefrom, the peg being adapted to be inserted into an aperture of a tether of a voice prosthesis device, wherein the collapsible portion of the elongated body is flexible to allow the elongated inserter body to be longitudinally collapsed to expose the peg of the rod for engagement with a strap of the voice prosthesis and the elongated inserter body is extendable from the collapsed position to extend over the peg.

2. The voice prosthesis insertion device according to claim 1, wherein the collapsible portion includes a pair of opposed openings in the elongated inserter body.

3. The voice prosthesis insertion device according to claim 1, wherein the elongated inserter body includes a pair of flats on the first end.

4. The voice prosthesis insertion device according to claim 1, wherein the first end of the elongated inserter body includes an aperture for receiving a stringer and the rod has a stringer attachment feature.

5. A voice prosthesis insertion device, comprising:
an elongated inserter body having a first end and a second end and including an aperture therein extending axially along the elongated inserter body, the elongated inserter body including a ring member at the second end that is supported by a pair of straps, wherein the elongated inserter body has at least one region between the first end and the second end that has an outer diameter that increases as the at least one region extends toward the second end, the elongated inserter body further having a collapsible portion defined by a pair of openings in the elongated inserter body; and
a rod disposed in the aperture of the elongated body, the rod including a first end and a second end and the second end including a flattened region with a peg extending from the flattened region, the peg being adapted to be inserted into an aperture of a tether of a voice prosthesis, wherein the collapsible portion of the elongated body is flexible to allow the collapsible portion to be longitudinally collapsed to expose the peg of the rod for engagement with a strap of the voice prosthesis and the collapsible portion is extendable from the collapsed portion to extend over the peg.

6. The voice prosthesis insertion device according to claim 5, wherein the collapsible portion includes a pair of opposed openings in the elongated body.

7. The voice prosthesis insertion device according to claim 5, wherein the elongated inserter body includes a pair of flats on the first end.

8. The voice prosthesis insertion device according to claim 5, wherein the first end of the elongated inserter body includes an aperture for receiving a stringer and the rod has a stringer attachment feature.

9. A method of loading a voice prosthesis into a voice prosthesis insertion device comprising;
forming a voice prosthesis insertion device including an elongated inserter body having a first end with a ring and a second end and including an aperture therein extending axially along the elongated inserter body, the elongated inserter body having a collapsible portion and a peg disposed in the aperture of the elongated body and covered by the elongated inserter body;
collapsing the collapsible portion of the elongated inserter body to cause a portion of the elongated inserter body to be retracted from the peg; inserting the peg into an aperture in a tether of a voice prosthesis and extending the collapsible portion of the elongated inserter body to cause the portion of the elongated inserter body to cover the peg; and
inserting a tubular body of the voice prosthesis through the ring.

* * * * *